US007226661B2

(12) United States Patent
Martinez

(10) Patent No.: US 7,226,661 B2
(45) Date of Patent: Jun. 5, 2007

(54) SYNTHESIS OF QUINONES AND PHENOLS ON SOLID SUPPORT

(75) Inventor: Luis E. Martinez, El Paso, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 404 days.

(21) Appl. No.: 10/357,317

(22) Filed: Feb. 3, 2003

(65) Prior Publication Data

US 2004/0151908 A1  Aug. 5, 2004

(51) Int. Cl.
  B01J 31/22  (2006.01)
  B01J 31/34  (2006.01)
  B32B 5/16  (2006.01)
(52) U.S. Cl. ........................ 428/403; 502/154
(58) Field of Classification Search ............... 502/154; 428/403
  See application file for complete search history.

(56) References Cited

U.S. PATENT DOCUMENTS

| | | | | |
|---|---|---|---|---|
| 3,627,700 | A * | 12/1971 | Zuech | 502/117 |
| 4,256,633 | A * | 3/1981 | Beffa | 534/690 |
| 4,331,559 | A * | 5/1982 | Banasiak | 502/154 |
| 4,820,309 | A * | 4/1989 | Holliger | 8/437 |
| 5,077,303 | A * | 12/1991 | Seele et al. | 514/336 |
| 5,296,595 | A * | 3/1994 | Doyle | 540/200 |
| 5,728,839 | A * | 3/1998 | Herrmann et al. | 548/103 |
| 6,177,464 | B1 * | 1/2001 | Cuny et al. | 514/530 |
| 6,380,266 | B1 * | 4/2002 | Katz et al. | 516/101 |
| 6,437,161 | B1 * | 8/2002 | Mihan et al. | 556/11 |
| 6,489,258 | B1 * | 12/2002 | Ying et al. | 502/60 |
| 6,515,155 | B1 * | 2/2003 | Klosin et al. | 556/11 |
| 6,538,115 | B2 * | 3/2003 | Cavell et al. | 534/15 |
| 7,026,266 | B2 * | 4/2006 | Chaudhari et al. | 502/155 |
| 2004/0109995 | A1 * | 6/2004 | Wakiya et al. | 428/328 |

FOREIGN PATENT DOCUMENTS

WO  WO 90/03374  4/1990

OTHER PUBLICATIONS

Maiorana et al., "Chrial nitrogen-stabilized Fischer carbene complexes: an efficient tool in the stereocontrolled elaboration of additional stereogenic centers", Pure Appl. Chem., vol. 71, No. 8, pp. 1453-1461, (1999).*
J. A. Connor, et al.; Reactions of [Acetoxy (2-furyl) carbene] Pentacarbonylchromium; *Journal of the Chemical Society* (A); 1971; pp. 3368-3372 ; vol. 21.
Bjorn C. Soderberg, et al.; Synthesis of Cyclobutanones by the Photolytic Reaction of Chromium Carbene Complexes with Olefins: Inter-and Intramolecular Reactions; *Journal of American Chemical Society* 1990; pp. 4364-4374; vol. 112.
Ayako Yamashita, et al.; Dihydronaphthoquinones, Hydroindoloquinones, Benzofurans, and Benzothiophenes as Inhibitors of 5-Lipoxygenase. Synthesis and Structure-Activity Studies; *Journal of Medicinal Chemistry*, 1990; pp. 775-781; vol. 33.
Noboru Fujii, et al.; Induction of Topoisomerase II-Mediated DNA Cleavage by the Plant Naphthoquinones Plumbagin and Shikonin; 1992; pp. 2589-2594; vol. 36, No. 12.
Shon R. Pulley, et al.; Solid-Phase, Solution, and Segment Condensation Peptide Syntheses Incorporating Chromium Carbene Complex-Derived Nonproteinogenic ("Unnatural") Amino Acid Fragments; *Journal of American Chemical Society*; 1993; pp. 9037-9047; vol. 115.
J.A. Summers et al.; Lipoxygenase Inhibitory Activity of U-66,858 and its Deacetylated Metabolite U-68,244 in Human Whole Blood; *Agents Actions*; 1994; pp. 32-36; vol. 41.
Gary C. Look, et al.; Methods for Combinatorial Organic Synthesis: The Use of Fast $^{13}C$ NMR Analysis for Gel Phase Reaction Monitoring; *Journal of American Chemical Society*; 1994; pp. 7588-7590; vol. 59.
William D. Wulff; Transition Metal Carbene Complexes: Alkyne and Vinyl Ketene Chemistry; pp. 469-547; vol. 12; *Comprehensive Organometallic Chemistry II: A review of the Literature 192-1994*; Elsevier Science Inc., Tarrytown, NY.
Keith Russell, et al.; Analytical Techniques for Combinatorial Chemistry; Quantitative Infrared Spectroscopic Measurements of Deuterium-Labeled Protecting Groups; *Journal of American Chemical Society*; 1996; pp. 7941-7945; vol. 118.
Susanta K. Sarkar et al.; An NMR Method to Identify Nondestructively Chemical Compounds bound to a Single Solid-Phase-Synthesis Bead for Combinatorial Chemistry Applications; *Journal of American Chemical Society*; 1996; pp. 2305-2306; vol. 118.
Zoi F. Plyta, et al.; Inhibition of Topoisomerase I by Naphthoquinone Derivatives; *Bioorganic & Medicinal Chemistry Letters* 8 (1998) pp. 3385-3390.

(Continued)

*Primary Examiner*—H. Thi Le
(74) *Attorney, Agent, or Firm*—Gardere Wynne Sewell LLP

(57) ABSTRACT

Generally, and in one form, the present invention is a method of making a benzene-modified compound on solid support that includes the steps of forming an (oxy)(aryl)carbene complex, esterifying the (oxy)(aryl)carbene complex to form an (ester)(aryl)carbene complex, and contacting the (ester)(aryl)carbene complex with a solid support such that the (ester)(aryl)carbene complex is bound to the solid support. In another form, the present invention includes compositions for the resulting (ester)(aryl)carbene complexes on solid support, such as any resulting solid support compounds formed after the initial coupling as well as those from any subsequent reaction, including those with linkers and on a solid support. The method and compositions of the present invention yield stable, durable, highly efficient and cost-effective as well as potentially biologically active lead compounds on solid support.

22 Claims, No Drawings

OTHER PUBLICATIONS

Stefano Maiorana, et al.; Synthesis of Polymer-Bound Fischer Chromium Alkoxy and Aminocarbene Complexes; Tetrahedron Letters; 1999; pp. 3635-3638; vol. 40.

Terumi Kagamizono, et al.; Phosphatoquinones A and B, Novel Tyrosine Phosphatase Inhibitors Produced by Streptomyces sp; *The Journal of Antibiotics*; 1999; pp. 75-80; vol. 52, No. 2.

James W. Herndon; The Use of Fischer Carbene Complexes for the Preparation of Five-Membered Carbocyclic Rings; *Tetrahedron*; 2000; pp. 1257-1280; vol. 56.

Steven P. Gygi, et al.; Quantitative Analysis of Complex Protein Mixtures Using Isotope-Coded Affinity Tags; Nature Biotechnology; Oct. 1999; pp. 994-999; vol. 17.

Armin de Meijere, et al.; FIscher Carbene Complexes as Chemical Multitalents: The Incredible Range of Products from Carbenepentacarbonylmetal $\alpha$, $\beta$-Unsaturated Complexes; *Angewandte Chemistry Int.*; 2000; pp. 3965-4002; vol. 39.

Masataka Itoigawa, et al.; Antitumor Agents. 203. Carbazole Alkaloid Murrayaquinone A and Related Synthetic Carbazolequinones as Cytotoxic Agents; *Journal of Natural Products*, Jul. 2000; pp. 893-897; vol. 63, No. 7.

Ray Bakhtiar, et al.; Mass Spectrometry of the Proteome; Molecular Pharmacology; 2001; pp. 405-415; vol. 60, No. 3.

Estrada Ay, et al.; Solid-Phase Synthesis of Substituted Quinones Compounds; presented at 224th American Chemical Society Meeting, Boston, MA; Aug. 12-22, 2002.

\* cited by examiner

SYNTHESIS OF QUINONES AND PHENOLS ON SOLID SUPPORT

TECHNICAL FIELD OF THE INVENTION

The present invention relates to combinatorial and solid phase organic chemistry, and more specifically to combinatorial chemistry as a tool for both chemical biology and drug discovery and as it relates to such areas as, for example, chemical genetics, genomics, and proteomics.

BACKGROUND OF THE INVENTION

The research carried out in the subject application was supported in part by grants from the University of Texas El Paso University Research Institute, Grant No. 14-5078-2551 and University of Texas El Paso Border Health Research, Grant No. 19-2750-5057.

Combinatorial chemistry is a critical tool in both chemical biology and drug discovery. The importance of combinatorial chemistry is increasing as the demand for libraries of small organic compounds grows. More recently, these libraries have become particularly useful to further the advances in fields such as chemical genetics, genomics and proteomics. Because of this demand, there is a need to develop more efficient strategies for the high-fidelity solid phase construction of chemical libraries, especially those that resemble natural products or known therapeutic compounds.

Lead compounds with the potential to progress as viable drug candidates have been identified from compound libraries using several strategies. Viable drug candidate strategies include rapid screening of large diverse collections, thematic libraries, project-directed libraries, and three-dimensional molecular models using corporate-derived drug databases. These strategies have also been used to identify potential therapeutic candidates then evaluated in controlled clinical trials.

More recent interest has developed in applying combinatorial chemistry techniques to the study of benzene and many of its derivatives. Compounds using traditional organic chemistry as well as solid phase organic chemistry have been isolated and used industrially as biologic reagents. Fused heterocyclic compounds are common in nature (e.g., purine) and are often biologically active and used as drugs to treat a wide variety of diseases. In addition, Fischer carbene complexes have been pursued in organic chemistry synthesis because of their strongly acidic hydrogens (ones alpha to the carbene carbon), strong electron-withdrawing power, and ease of deprotonation. The strong electrophilic property of moieties such as $Cr(CO)_5$ make them particularly useful in the synthesis of organic compounds as their deprotonation results in a metal "enolate" that is especially reactive with electrophilic reagents. The present invention exploits this property by using these moieties to prepare a whole new host of organic compound libraries that may serve as potential lead compounds.

Most recently, research has suggested that it may be possible to immobilize chromium carbene complexes with polymer-supported tripeptide and triphenyl phosphine. These complexes, however, remain limited in their ability to generate lead compounds as they are merely complexes formed in a series of reactions to create organic compounds with potential biological activity. To date, no one has described the use of polymer bound chromium (Cr) carbene complexes for the synthesis of any compound library for any reaction.

The present invention has met this need by creating active scaffolds and has also allows the scaffolds to include a one-step oxidation and cleavage process that is desirable for high throughput and parallel processing of potential biologically active compounds. The approach centers on linking the carbene complex directly onto the solid support through the oxygen of the carbene. The process allows for subsequent modifications of an attached phenol that leads to a large diversity of products. More importantly, the present invention is unique from the earlier attempts to create a class of biologically active scaffolds for combinatorial and solid phase organic chemistry.

The benefits of the present invention include the generation of a new class of biologically active scaffolds that encompass essential features of combinatorial chemistry. The present invention is able to both use the microenvironment of the solid support for synthesis of the desired compound and as reactant. The microenvironment may serve as both solid-phase reagent and a traceless linker. In addition, potentially biologically active compounds are cleaved off the solid support in a one-step parallel process.

SUMMARY OF THE INVENTION

In order to produce stable, durable, highly efficient and cost-effective lead compounds in solid support with biologic activity, there is a need for improved reactions that produce compounds on solid support that are synthesized and cleaved in parallel and are also potentially biologically active. The present invention includes a metal-mediated benzannulation reaction on solid support in which the microenvironment of the solid support is used to modify the reactivity and favor the synthesis of the desired compound. The linker to which the carbene or phenol compound is linked does serve as a reagent and, more specifically, as a traceless linker. The microenvironment provides a number of advantages not obtainable in solution phase. Applications that may benefit from the use of with the present invention include previously unobtainable combinatorial and solid phase organic chemistry in solid support.

Generally, and in one form, the present invention is a method of making a benzene-modified compound on solid support that includes the steps of forming an (oxy)(aryl) carbene complex, esterifying the (oxy)(aryl)carbene complex to form an (ester)(aryl)carbene complex; and contacting the (ester)(aryl)carbene complex with a solid support such that the (ester)(aryl)carbene complex is bound to the solid support. The (ester)(aryl)carbene complex is bound to the solid support via a transesterification or amidation reaction.

In another form, the present invention is a method of modifying the compounds of the present invention by using a "reverse" reaction comprising the step of contacting a polymer-bound acetylene containing molecule and an aryl methylene pentacarbonyl complex compound. The acetylene may include substitutions that are symmetrical, unsymmetrical and functionalized, as examples.

In still another form, the present invention is a method of cleaving a polymer-bound benzannulated compound in order to form a free quinone. The quinone is liberated by the addition of an oxidizing agent, such as ceric ammonium nitrate, $O_2$, $FeCl_2$, as examples.

Another form of the present invention is the concomitant oxidation and liberation of an epoxy quinone by treating a polymer-bound benzannulated compound with a solution of sodium hypochlorite. Additional oxidative cleavage reagents (oxidants) that may be applied include, but are not limited to, chiral oxidants and chiral epoxidation catalysts.

In another form, the present invention includes compositions for the resulting (ester)(aryl)carbene complexes on solid support, such as any resulting solid support compounds formed after the initial coupling as well as those from any subsequent reaction, including those with linkers and on a solid support. Examples of solid supports include polystyrene beads, plastic, glass, gold and other metals, etc. The resulting (ester)(aryl)carbene complexes on solid support occur via a transesterification or amidation reaction.

Other features and advantages of the present invention shall be apparent to those of skill in the art upon reference to the following detailed description taken in conjunction with the accompanying drawings, and such subject matter constitutes a portion of the present invention.

DETAILED DESCRIPTION OF THE INVENTION

While making and using various embodiments of the present invention are discussed herein in terms of combinatorial and solid phase organic chemistry, it should be appreciated that the present invention provides many applicable inventive concepts that can be embodied in a wide variety of specific contexts. The specific embodiments discussed herein are merely illustrative of specific ways to make and use the invention, and do not limit the scope of the invention.

To facilitate the understanding of this invention, a number of terms are defined below. Terms defined and used herein have meanings as commonly understood by a person of ordinary skill in the areas relevant to the present invention. Terms such as "a," "an," and "the" are not intended to refer to only a singular entity, but include the general class of which a specific example is used for illustration. The terminology herein is used to describe specific embodiments of the invention, but their usage does not limit the invention, except as outlined in the claims.

As used throughout the present specification the following abbreviations and symbols are used: THF, tetrahydrofuran; elements are identified either by name or by their accepted symbol as found in the Periodic Table of the Elements.

All technical and scientific terms used herein have the same meaning as commonly understood by one of ordinary skill in the art to which this invention belongs, unless defined otherwise. All publications mentioned herein are incorporated herein by reference to disclose and describe the methods and/or materials in connection with which the publications are cited.

The present invention includes the synthesis of polymer bound metal carbene complexes and their benzannulation. The benzannulation may be accomplished either thermally or with application of microwave energy. The present invention includes the compositions and method of making Compounds 4–17, as representative compounds. Solid support used in the method of making these compounds may include any type, such as polymer beads, pins, silica, sand, glass, and any and all surfaces. In addition, each position around the Compound 4 and 5 ring may be substituted either alone, or in combination with one or more of the remaining positions. Compound 6 is generally synthesized using solid-phase organic synthesis.

Examples of the compounds and methods of generating the compounds of the present invention are presented below. Scheme 1 is the general method of synthesis used to generate a representative compound as depicted by Compound 1.

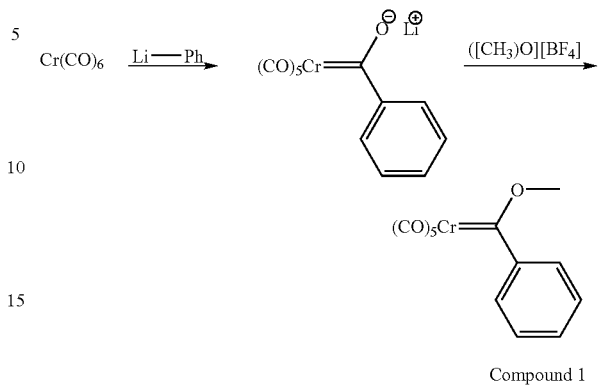

Compound 1

Example of Pentacarbonyl(methoxyphenylmethylene)Chromium (0)

To a stirred suspension of chromium hexacarbonyl (3 g, 9.62 mmol) in dry THF (175 mL) at 0 degrees Centigrade was added a solution of phenyllithium (8.72 mL, 1.8 M solution in hexanes, 11.06 mmol) over 30 minutes. After 2 hours the solution was removed in vacuo and the resulting brown residue was dissolved in nitrogen-saturated water. Trimethyloxonium tetrafluoroborate (1.139 g, 7.696 mmol) was added and the aqueous layer was then extracted with ether (3×10 mL). The organic layers were collected and dried over magnesium sulfate. The solvent was removed in vacuo and chromatographic purification was performed on silica gel (eluent:dichloromethane-hexanes is 1:9; Rf=0.40) and yielded Compound 1 as an orange red solid (2.5 g, 60%).

Results of $^1$H NMR(CDCl$_3$) were the following: δ 7.53–7.38 (m, 3H, Ar—H); 7.32–7.21 (m, 2H, Ar—H); 4.72 ppm (s, 3H, OCH$_3$). FT-IR (KBr pellet): 2062, 1978, 1946 (Cr—CO); 1258 ($C_{carbene}$—O). Literature data[37]: $^1$H NMR (250 MHz, CDCl$_3$): δ 7.53–7.38 (m, 3H,); 7.32–7.21 (m, 2H,); 4.72 ppm (s, 3H,). FT-IR (CH$_2$Cl$_2$): 2075, 1993, 1940.

Example of Tetramethylammonium Salt of [(oxy)(aryl)Carbene] Pentacarbonylchromium (0)

To a stirred suspension of chromium hexacarbonyl (3 g, 9.62 mmol) in dry THF (175 mL) at 0 degrees Centigrade was added a solution of phenyllithium (8.72 mL, 1.8 M solution in hexanes, 11.063 mmol). The addition was slow over a 30 minute time period. After at least about two hours the solution was removed in vacuo and the resulting brown residue dissolved in nitrogen-saturated water. Tetramethylammonium bromide (1.71 g, 10.582 mmol) was added under nitrogen. The solution was stirred for 20 minutes at 0° C. and extracted with dichloromethane 3×10 mL. The dichloromethane extracts were dried over MgSO$_4$ and the solvent was removed in vacuo to afford yellow orange solid Compound 2 (4.43g, 86%). The product was used for solid phase synthesis without further purification, where the FT-IR (KBr pellet) was: 2032, 1947, 1904, 1875, 1859 (Cr—CO); 1144 ($C_{carbene}$—O).

An example of Compound 2 and Compound 3 as used in the present invention to generate Compound 4, another representative compound, are all illustrated in SCHEME 2. Compound 3 exemplifies an (ester)(aryl)carbenemetal complex of the present invention. The dark spheres in this and other molecular structures represent a solid support. Compound 3 generates Compound 4 via a transesterification reaction upon attachment to the solid support.

SCHEME 2

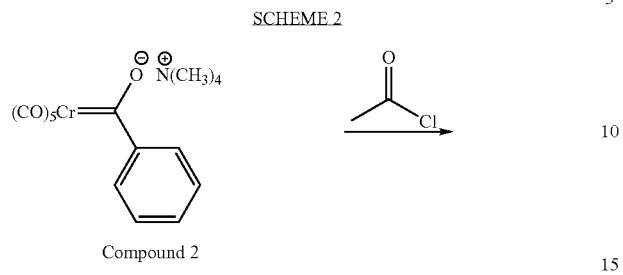

Compound 2

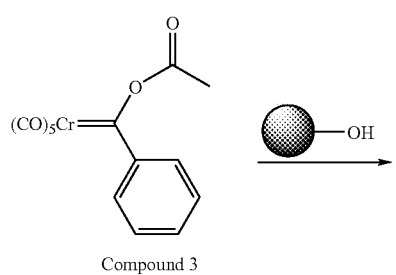

Compound 3

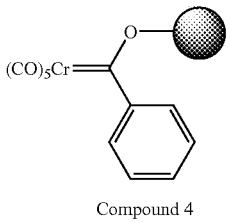

Compound 4

Example of Pentacarbonyl(phenylmethylene)Chromium(0) Linked on Argopore Beads A 50 mL flask fitted with an airfree adapter, a rubber septum, and a stirring bar were charged with 150 mg (0.405 mmol, 6.2 equivalents) tetramethylammonium salt of [(oxy)(aryl)carbene]pentacarbonylchromium and 20 mL THF (0.27 M). The yellow solution was cooled to −40 degrees Centigrade using slush bath made from the mixture of liquid nitrogen and acetone. 40 μL (0.423 mmol) of acetyl chloride was slowly injected into the system. The mixture was stirred at −20 degrees Centigrade for 1 hour and the color turned from orange red to dark red indicating the formation of Compound 3, an example of an (ester)(aryl)carbene complex. Additional examples of (ester)(aryl)carbene complexes on solid support are shown below.

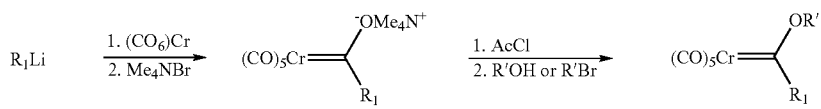

Structures of $R_1$

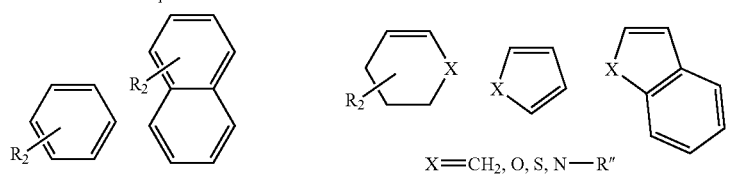

$X = CH_2, O, S, N-R''$

Structures of $R_2$ $OCH_3$, alkyl, aryl, COR, $CO_2R$, NHR'', $NO_2$

Structures of R′

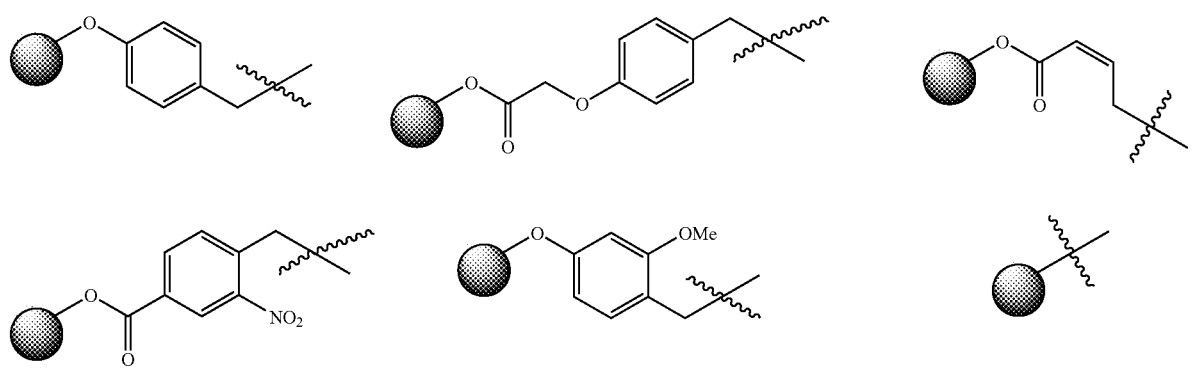

Following the formation of Compound 3, the solvent was removed and 100 mg Argopore (0.065 mmol, loading 0.65 mmol/g) resin (as an example of a solid support) was added under nitrogen. After adding 1.5 mL dry THF, the system was shaken on a wrist shaker for 40 minutes until the red color of solution was discharged and the beads became red. The beads were washed with 4×5 mL THF and 4×5 mL CH$_2$Cl$_2$ (five times each) to afford orange red beads.

Results of FT-IR (thin film) were: 2062, 1947 (Cr—CO). Studies have also been performed and the present invention may be applied by using a wide variety of additional solid support structures in addition to Argopore beads, including Argogel, Tentagel, and plain polystyrene, as prototypical examples.

SCHEME 3 depicts the preparation of Compounds 5 and 6 from Compound 4 using methods of the present invention.

SCHEME 3

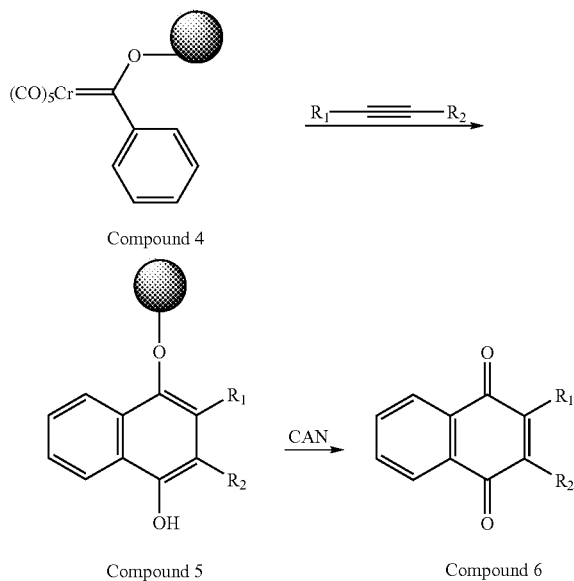

Compound 4

Compound 5

Compound 6

Example of Benzannulation Reaction on Solid Support Using Normal Glassware

Following the synthesis of Compound 4, as a representative compound, at least about 0.65 mmol equivalents acetylene and 1.5 mL THF (0.43 M) were added to the system. The whole system was shaken for at least about 12 hours at 60 degrees Centigrade. The green beads were washed with THF (5×5 mL) and CH$_2$Cl$_2$ (5×5 mL). Then 10 equivalents cerric ammonium nitrate (CAN) dissolved in 1 mL water and mL acetonitrile was added to the beads and stirred for 5 hours. The beads were filtered and the liquid was collected and extracted with CH$_2$Cl$_2$ (3×10 mL). After drying the liquid over Mg$_2$SO$_4$, the mixture was concentrated to yield yellow residues.

The compound 2,3-Phenyl-1,4-naphthoquinone is derived as a yellow solid. Spectra results were as follows: $^1$H NMR (CDCl$_3$) δ 7.08 (m, 6H), 7.24 (m, 2H), 7.80 (dd,=3.4 Hz and J=5.1 Hz, 2H), 8.21 (dd, J=3.4 Hz and J=5.1 Hz, 2H).

Example of Performing the Benzannulation Reaction in "Reverse"

In addition to the solid phase benzannulation reaction presented above that includes immobilization of a Cr carbene complex, the solid phase benzannulation reaction may be used to immobilize an alkyne. This method is used to generate Compounds 7 and 8, as representative compounds of the present invention, wherein the linked heteroatom may be any atom, such as, e.g., N, Si, P, Se, C, O, etc. SCHEME 4 is provided to illustrate an example of the compositions and methods of preparing Compounds 7 and 8, considered to be a solid phase benzannulation reaction in reverse.

SCHEME 4

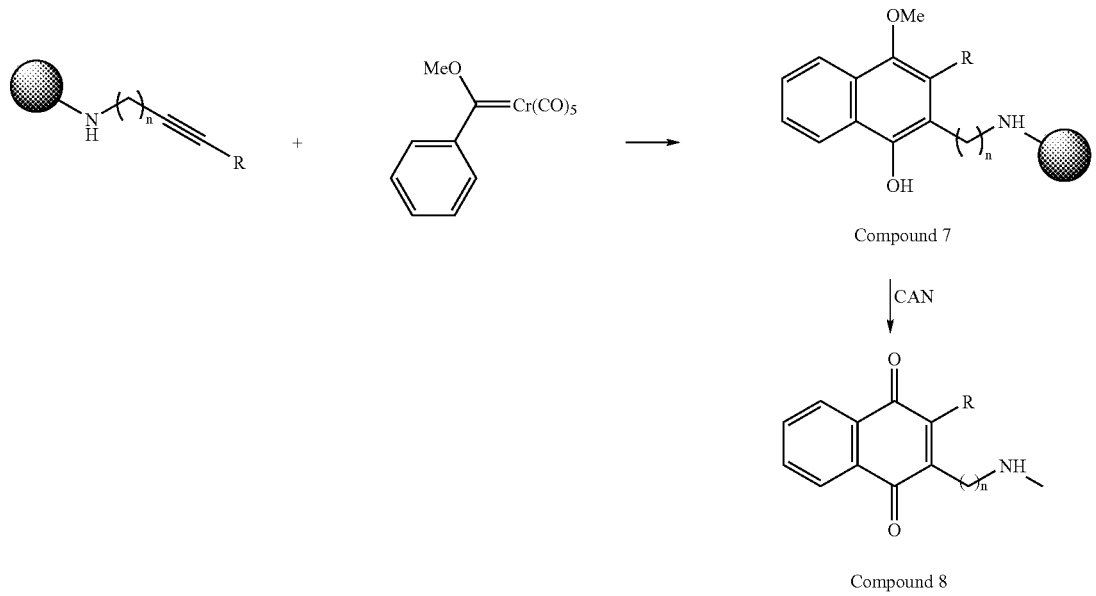

Compound 7

Compound 8

Example of Further Functionalization of the Napthoquinone Core

A further embodiment of the present invention uses an environmentally benign oxidation reagent, such that oxidation of the benzannulated product Compound 9 with common bleach, proceeds cleanly to the epoxyquinone product of Compound 10 with a 76% yield as shown in SCHEME 6. This is the first report using bleach as an oxidant for the benzannulation of Fischer carbenes.

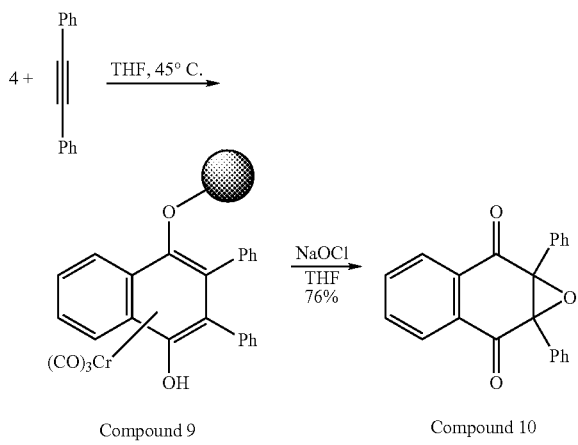

Compound 9    Compound 10

For solid phase organic synthesis (SPOS), the bleach-oxidation method of the present invention provides another means of introducing additional diversity around the quinone scaffold, because this reaction is highly favorable on solid support. As before, any type of solid support may be used, including polymer beads, pins, silica, sand, glass, of any and all surfaces. The solution phase analog of the reaction may be messy and low yielding.

Additional Library Diversity Elements

The chromium-mediated benzannulations on solid support produce may differentially deprotected phenol libraries (see as an example Compound 18 as a representative compound) prior to oxidative cleavage to a quinone, as represented by Compound 19, as an example. With the present invention, additional SPOS (Solid Phase Organic Synthesis) reactions for the incorporation of additional diversity elements utilizing Compound 18 as a general scaffold may also be pursued. For example, each set of parallel reactions described in Scheme 8 for the synthesis of phenol libraries of, for example, Compound 18, may be reacted with a variety of additional reagents to incorporate further diversity as shown in Scheme 7. With such processing, the entry to additional small molecule classes that are currently unattainable through current SPOS methods is readily attained.

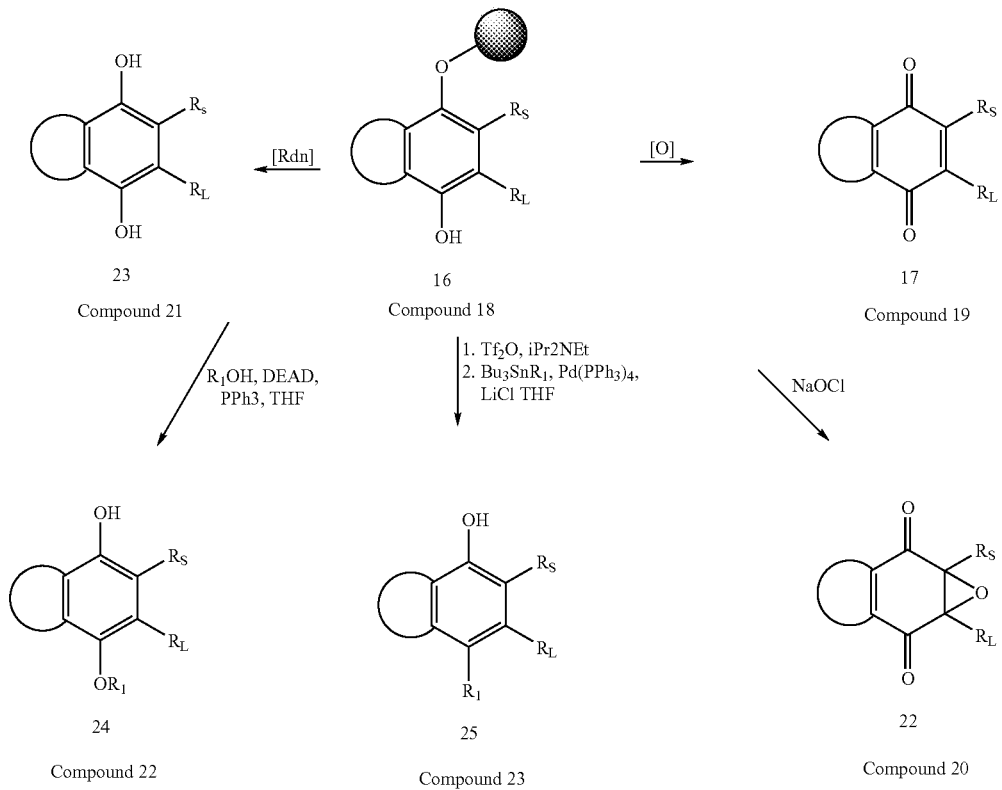

SCHEME 7

Utilizing bleach as an example of a oxidative cleavage reagent in the present invention, the reaction may be used to produce epoxyquinone (see, for example Compound 10 as a representative compound). Further, this mild, novel methodology is used to generate epoxyquinone compound libraries, as shown for example in Compound 20 as a representative compound, from the polymer supported benzannulation products of Compound 18 as described above. Additional oxidative cleavage reagents (oxidants) that may be applied include, but are not limited to, chiral oxidants and chiral epoxidation catalysts.

Building upon the initial SPOS of a 2,3-diphenyl-1,4 naphthalenediol, as a representative example, and, in addition to oxidative cleavage strategies for the utilization of compounds such as Compound 18, deprotection strategies to produce 1,4-diphenol libraries may be applied. Standard reductive benzyl and 4-methyoxybenzyl ether deprotection strategies (e.g., TFA, PhSCH$_3$, BF$_3$-Et$_2$O, EtSH, BBr$_3$, Me3SiI, lithium triethylborohydride, etc., as examples) may be used to produce 1,4-diphenol libraries, as represented by Compound 21.

Most importantly, from the perspective of incorporating additional diversity elements, the synthesis of compounds represented by Compound 18 allows for a combinatorial alkylation of the free phenol. The Mitsunobu reaction is one of the most utilized for the synthesis of diverse aryl ethers, in particular its mild conditions make it ideally suited for solid-phase synthesis. As a further advantage, it is possible to then alkylate compounds represented by Compound 18 under Mitsunobu conditions with a wide variety of primary and secondary alcohols to generate differentially protected 4-alkoxyphenol libraries, see for example Compound 22 as an example, following cleavage off of the solid support.

Furthermore, to display further functionality, the 4-alkoxyphenol product of Compound 18 from these reactions can be activated in situ as an aryl triflate, subjected to Stille coupling with a diverse array of aryl and vinyl tin compounds, and cleaved off the solid support to form phenol libraries similar to those represented by Compound 23, where all positions around the resulting benzene ring can be diversified.

Example of SPOS (Solid Phase Organic Synthesis) of Specific Targets

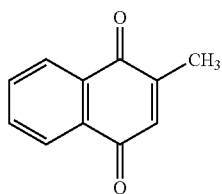

Compound 11

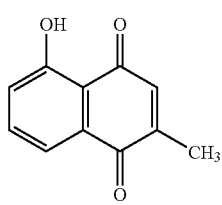

Compound 12

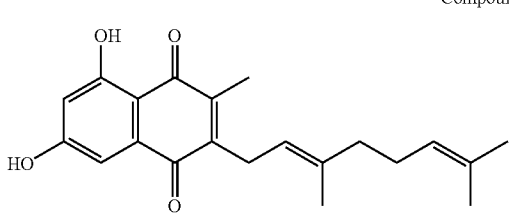

Compound 13

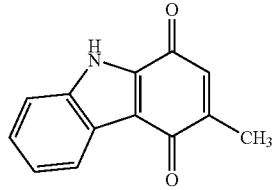

Compound 14

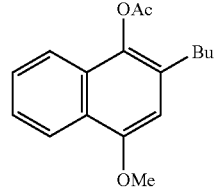

Compound 15

Representative examples of compounds obtainable on solid phase using the methods of the present invention include: vitamin K3 (menadione) (Compound 11, that in one embodiment may be used as an anticancer drug); plumbagin (Compound 12, an inhibitor of topoisomerase I and II); phosphatoquinone B (Compound 13, a novel tyrosine phosphatase inhibitor); Murrayaquinone A (Compound 14, a carbazole alkaloid with significant cytotoxicity against SK-MEL-5 and Colo-205 cells); and U66,858 (Compound 15, an inhibitor of leukotriene synthesis and 5-lypoxygenase with potential use for the treatment of asthma or deep vein thrombosis).

The use of the methodology of the present invention will lead to the first synthesis of chemicals and compounds with extremely diverse biological activity as scaffolds on solid support.

Example of Solid Phase Synthesis of Stable Isotope Labeled Quinones and Vitamin K Analogs Reagents labeled with stable isotopes ($^{13}$C, $^{2}$H, $^{15}$N, etc.) have been used in SPOS as a method to monitor and characterize solid-phase reactions. The present invention includes a complementary method of monitoring the reaction on the solid support through the synthesis of $^{13}$C-labeled quinones and their Fischer carbene precursors on solid support. Recent advancements in high-throughput proteome characterization using mass spectrometry and NMR protein structure elucidation make the synthesis of compounds of the present invention (especially ones that are labeled with one or more stable isotopes) in great demand.

SCHEME 8

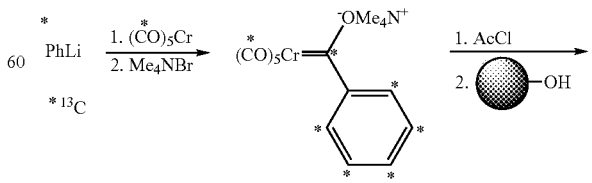

*$^{13}$C

-continued

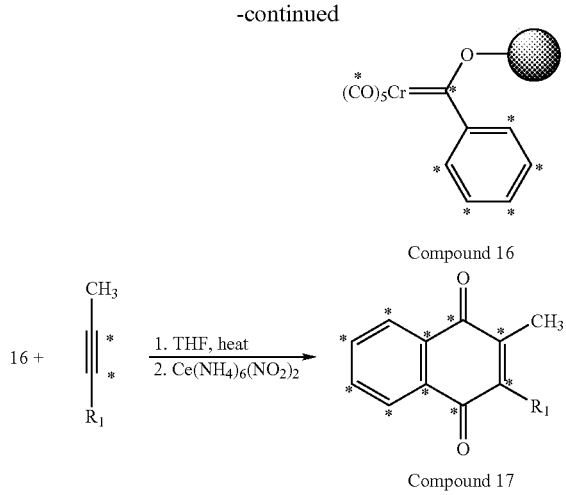

Compound 16

Compound 17

Representative Examples
R1 = H (Vitamin K3), Me, Et, Pr, Ph, OR, (CH2)nSR

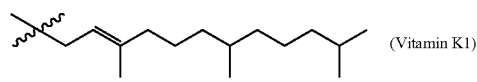 (Vitamin K1)

For example, SCHEME 8 shows the synthesis of $^{13}$C-labeled vitamin K libraries in which a synthetic route analogous to the one described previously is used. In SCHEME 8, $^{13}$C-labeled precursors are used, e.g., $^{13}$C-labeled chromium hexacarbonyl and phenyllithium are combined in order to produce a solid supported Fischer carbene complex (Compound 16) where all the carbons are $^{13}$C-labeled. Subsequent benzannulation with appropriate substituted acetylenes produces one or more $^{13}$C-labeled vitamin K analogs (Compound 17). Other examples of compounds as described in the present invention using one or more stable compounds may be synthesized as in SCHEME 7.

While specific alternatives to steps of the invention have been described herein, additional alternatives not specifically disclosed but known in the art are intended to fall within the scope of the invention. Thus, it is understood that other applications of the present invention will be apparent to those skilled in the art upon reading the described embodiment and after consideration of the appended claims and drawing.

What is claimed:

1. A composition comprising:
   an (ester)(aryl)carbenemetal complex attached to a solid support, wherein attachment is via a transesterification or amidation reaction.

2. The composition of claim 1, wherein the solid support is a polymer.

3. The composition of claim 2, wherein the complex is formed by contacting the complex attached to a polymer and an acetylene molecule.

4. The composition of claim 1, wherein the composition is further cleaved by an oxidant to release a quinone.

5. A method of preparing a composition of claim 1 comprising the step of:
   attaching an (ester)(aryl)carbenemetal complex to a solid support, wherein attachment is via a transesterification or amidation reaction.

6. A composition comprising:
   an (ester)(aryl)carbenemetal complex attached to a solid support via a linker, wherein attachment is via a transesterification or amidation reaction.

7. The composition of claim 6, wherein the solid support is a polystyrene bead.

8. The composition of claim 6, wherein the solid support is a plastic bead.

9. The composition of claim 6, wherein the solid support is a metallic surface.

10. The composition of claim 6, wherein the solid support is a glass surface or bead.

11. The composition of claim 6, wherein the linker is an oxygen atom.

12. The composition of claim 6, wherein the linker is a silicon atom.

13. The composition of claim 6, wherein the linker is a sulfur atom.

14. The composition of claim 6, wherein the linker is an amino or an imido group.

15. The composition of claim 6, wherein the metal is chromium, molybdenum or tungsten.

16. The composition of claim 6, wherein the composition has a structure comprising

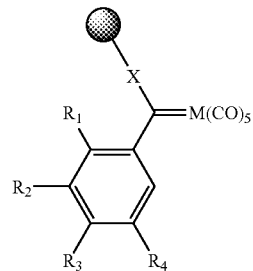

wherein the solid support is symbolized by the dark circle; M is Cr, Mo or W; X symbolizes the linker, each R group may independently be chosen from alkyl, aryl or hydrogen in any combination.

17. The composition of claim 6, wherein one or more of the atoms in the composition is substituted with a stable isotopic label.

18. The composition of claim 17, wherein the stable isotopic label is selected from the group consisting of deuterium and carbon-13.

19. The composition of claim 6, wherein the solid support is a polymer.

20. The composition of claim 19, wherein the complex is formed by contacting the complex attached to a polymer and an acetylene molecule.

21. The composition of claim 6, wherein the composition is further cleaved by an oxidant to release a quinone.

22. A method of preparing a composition of claim 6 comprising the step of:
   attaching an (ester)(aryl)carbenemetal complex to a solid support via a linker, wherein attachment is via a transesterification or amidation reaction.

* * * * *